US010675072B2

(12) United States Patent
Ananthan et al.

(10) Patent No.: US 10,675,072 B2
(45) Date of Patent: Jun. 9, 2020

(54) BONE FIXATION WITH A PLATE AND A COUPLER CONNECTED BY FLEXIBLE MEMBERS

(71) Applicant: Acumed LLC, Hillsboro, OR (US)

(72) Inventors: Bharadwaj Ananthan, Portland, OR (US); Amir Meir Matityahu, Los Altos, CA (US); Thomas R. Lyon, Brooklyn, NY (US); Andrew Howard Schmidt, Orono, MN (US); David William Vanvleet, Hillsboro, OR (US)

(73) Assignee: Acumed LLC, Hillsboro, OR (US)

( * ) Notice: Subject to any disclaimer, the term of this patent is extended or adjusted under 35 U.S.C. 154(b) by 191 days.

(21) Appl. No.: 15/860,436

(22) Filed: Jan. 2, 2018

(65) Prior Publication Data

US 2019/0201064 A1  Jul. 4, 2019

(51) Int. Cl.
*A61B 17/82* (2006.01)
*A61B 17/80* (2006.01)

(52) U.S. Cl.
CPC .......... *A61B 17/82* (2013.01); *A61B 17/8004* (2013.01); *A61B 17/809* (2013.01); *A61B 17/8023* (2013.01); *A61B 17/8057* (2013.01); *A61B 17/8061* (2013.01)

(58) Field of Classification Search
CPC ..... A61B 17/02; A61B 17/80; A61B 17/8004; A61B 17/8057; A61B 17/809; A61B 17/8061
See application file for complete search history.

(56) References Cited

U.S. PATENT DOCUMENTS

| 4,889,110 | A | * | 12/1989 | Galline | .............. | A61B 17/1796 |
| | | | | | | 606/916 |
| 5,993,452 | A | | 11/1999 | Vandewalle | | |
| 6,066,141 | A | | 5/2000 | Dall et al. | | |
| 6,338,734 | B1 | | 1/2002 | Burke et al. | | |
| 6,960,213 | B2 | | 11/2005 | Chervitz et al. | | |
| 7,255,701 | B2 | | 8/2007 | Allen et al. | | |

(Continued)

FOREIGN PATENT DOCUMENTS

| EP | 0955013 A1 | 10/1999 |
| WO | 2012007910 A1 | 1/2012 |

OTHER PUBLICATIONS

Smith & Nephew, "Accord Cable System", May 2008, pp. 1-16.
Stryker, "Dall-Miles® Cable System Surgical Protocol", 2007, 16 pages.
Synthes®, "The Orthopaedic Cable System Technique Guide", 2003, 24 pages.

(Continued)

*Primary Examiner* — Christopher J Beccia
(74) *Attorney, Agent, or Firm* — K&L Gates LLP

(57) ABSTRACT

Apparatus and method for fixing a bone using a plate and a coupler that are connected to one another with flexible members. The plate may be configured to be attached to a shaft region of a bone. The coupler may be configured to be disposed on an end region of the bone, and may define a bore and an aperture. The flexible members may include a first flexible member and a second flexible member, each including a wire or cable. The first flexible member may be configured to extend from the plate, through the bore, and back to the plate. The second flexible member may be configured to extend from the plate to the coupler on a path that approaches the coupler transverse to a line that is parallel to the bore. The apparatus and method may be used to stabilize the greater trochanter of a femur.

19 Claims, 7 Drawing Sheets

(56) References Cited

U.S. PATENT DOCUMENTS

| | | | |
|---|---|---|---|
| 7,476,255 B2 | 1/2009 | Lester et al. | |
| 7,611,513 B2 | 11/2009 | Deloge et al. | |
| 8,343,155 B2 | 1/2013 | Fisher et al. | |
| 8,574,235 B2 | 11/2013 | Stone | |
| 8,764,809 B2 * | 7/2014 | Lorenz | A61B 17/74 606/286 |
| 8,894,693 B2 | 11/2014 | Petit et al. | |
| 8,906,072 B2 | 12/2014 | Norris et al. | |
| 9,138,268 B2 | 9/2015 | Cavallazzi et al. | |
| 9,662,219 B2 | 5/2017 | Bonin, Jr. et al. | |
| 2004/0087954 A1 * | 5/2004 | Allen | A61B 17/82 606/74 |
| 2005/0171544 A1 | 8/2005 | Falkner, Jr. | |
| 2006/0058795 A1 | 3/2006 | Boyd | |
| 2008/0234679 A1 | 9/2008 | Sarin et al. | |
| 2009/0312758 A1 | 12/2009 | Petit et al. | |
| 2017/0135738 A1 | 5/2017 | Baumgartner | |

OTHER PUBLICATIONS

Synthes®, "Trochanter Stabilization Plate for DHS. Extends DHS Construct to Help Stabilize Greater Trochanter. Technique Guide", 2000, 16 pages.

Zimmer, "Cable-Ready® Cable Grip System Cable Buttons Data Sheet", 2012, 2 pages.

Zimmer, "Cable-Ready® Greater Trochanteric Reattachment Surgical Technique", 2010, 12 pages.

Thomas, Shane, Authorized Officer, ISA/US Commissioner for Patents, "International Search Report" in connection with related International Application No. PCT/US2018/068001, dated Mar. 15, 2019, 2 pgs.

Thomas, Shane, Authorized Officer, ISA/US Commissioner for Patents, "Written Opinion of the International Searching Authority" in connection with related International Application No. PCT/US2018/068001, dated Mar. 15, 2019, 4 pgs.

* cited by examiner

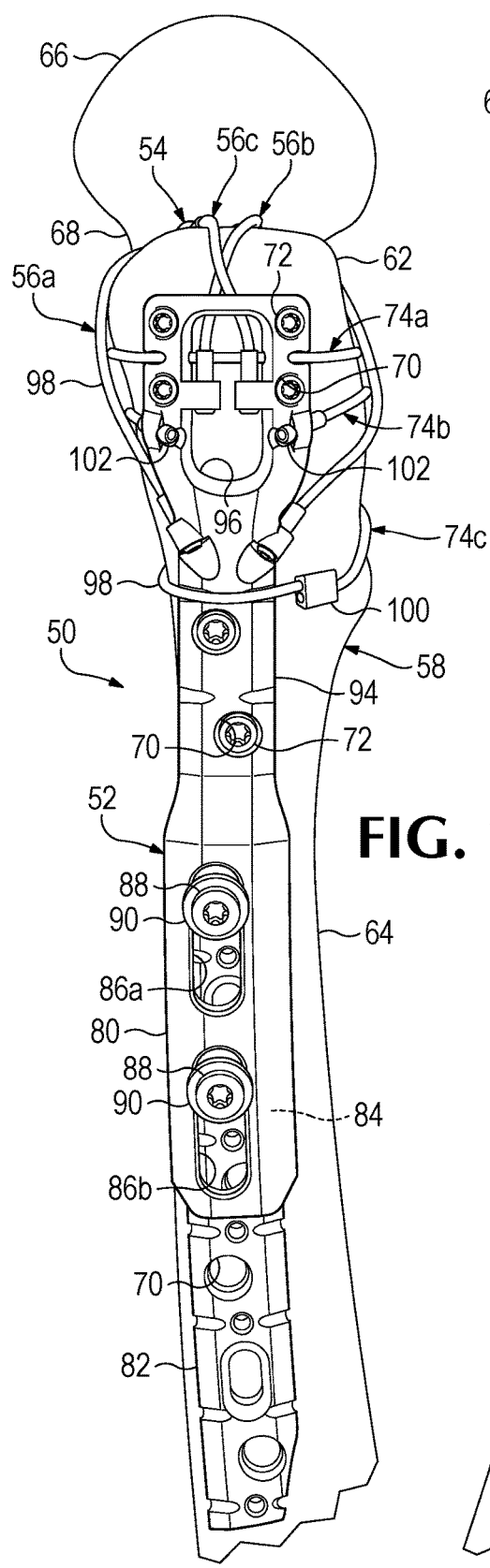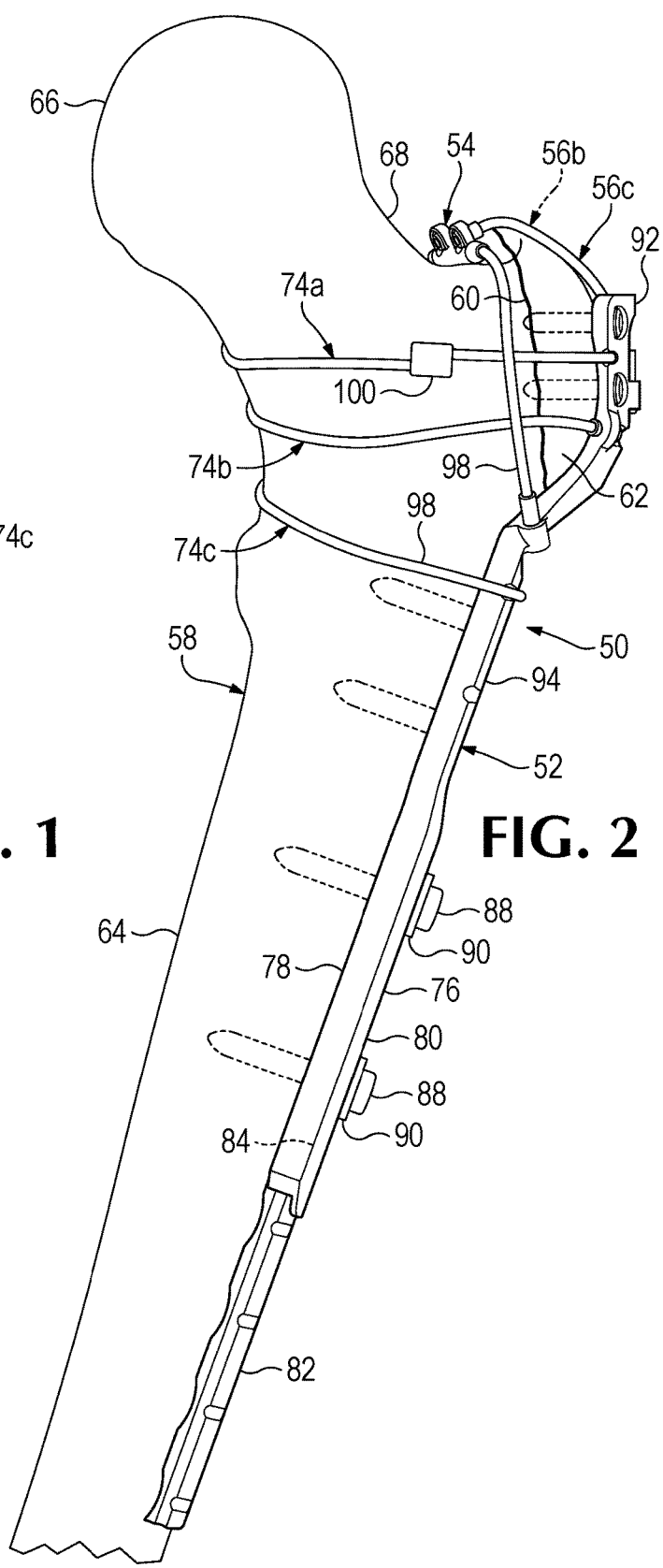

US 10,675,072 B2

BONE FIXATION WITH A PLATE AND A COUPLER CONNECTED BY FLEXIBLE MEMBERS

A fractured long bone can be fixed with an elongated bone plate secured to the bone with fasteners, such as bone screws. However, in some cases, trauma can create a relatively small bone fragment containing a site of major muscle insertion. The muscle(s) may obstruct placement of the plate onto bone and can apply strong displacement forces to the fragment, rendering fixation particularly problematic.

An example of this type of injury is a fracture involving the greater trochanter of the femur. The greater trochanter is a lateral protuberance to which various muscles attach, such as gluteal muscles. Abduction of the femur is driven by force applied to the greater trochanter by the gluteal muscles. When fracture of the femur separates a significant portion of the greater trochanter from the rest of the femur, stabilization of the greater trochanter can be challenging.

SUMMARY

The present disclosure provides apparatus and method for fixing a bone using a plate and a coupler that are connected to one another with flexible members. The plate may be configured to be attached to a shaft region of a bone. The coupler may be configured to be disposed on an end region of the bone, and may define a bore and an aperture. The flexible members may include a first flexible member and a second flexible member, each including a wire or cable. The first flexible member may be configured to extend from the plate, through the bore, and back to the plate. The second flexible member may be configured to extend from the plate to the coupler on a path that approaches the coupler transverse to a line that is parallel to the bore. The apparatus and method may be used to stabilize the greater trochanter of a femur.

BRIEF DESCRIPTION OF THE DRAWINGS

FIG. 1 is a lateral view of a fractured left femur fixed with an exemplary fixation apparatus including a plate connected to a coupler using flexible members, in accordance with aspects of the present disclosure.

FIG. 2 is an anterior view of the left femur of FIG. 1 being fixed with the fixation apparatus of FIG. 1.

DETAILED DESCRIPTION

The present disclosure provides apparatus and method for fixing a bone using a plate and a coupler that are connected to one another with flexible members. The plate may be configured to be attached to a shaft region of a bone. The coupler may be configured to be disposed on an end region of the bone, and may define a bore and an aperture. The flexible members may include a first flexible member and a second flexible member, each including a wire or cable. The first flexible member may be configured to extend from the plate, through the bore, and back to the plate. The second flexible member may be configured to extend from the plate to the coupler on a path that approaches the coupler transverse to a line that is parallel to the bore. The apparatus and method may stabilize the greater trochanter of a femur.

Further aspects of the present disclosure are described in the following sections: (I) fixation apparatus with plate and coupler, (II) methods of bone fixation, (III) composition of apparatus components, and (IV) examples.

I. Fixation Apparatus With Plate and Coupler

This section describes an exemplary fixation apparatus 50 utilizing a plate 52, a coupler 54 (interchangeably termed an anchor), and a plurality of tensioned flexible members 56a-56c connecting the plate and the coupler to one another; see FIGS. 1-10.

Figure 3:
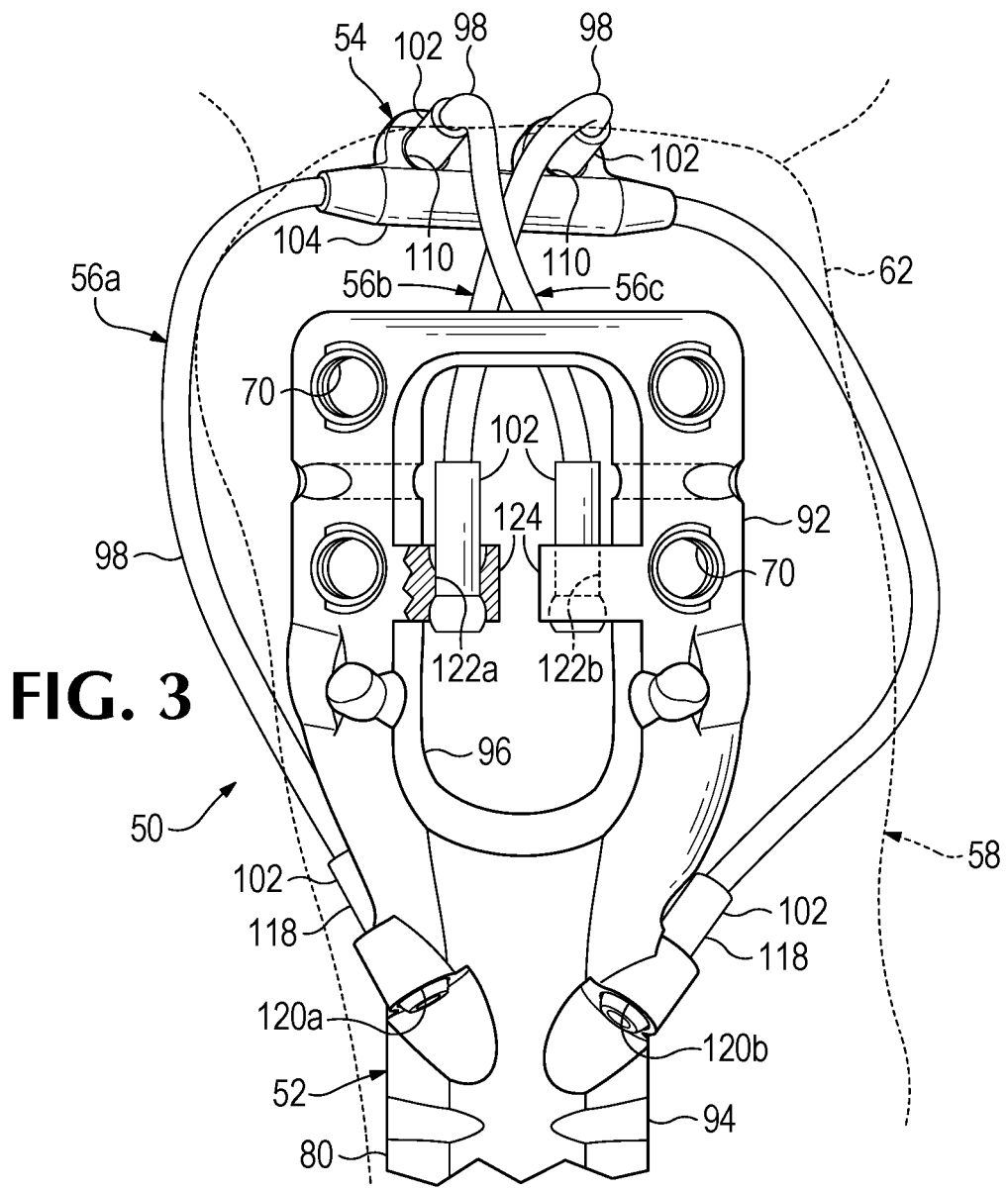
FIG. 3 is a fragmentary view of selected aspects of the fixation apparatus and femur of FIG. 1, taken around the coupler and a proximal end of the plate, with the femur shown in dashed outline.
Figure 4:
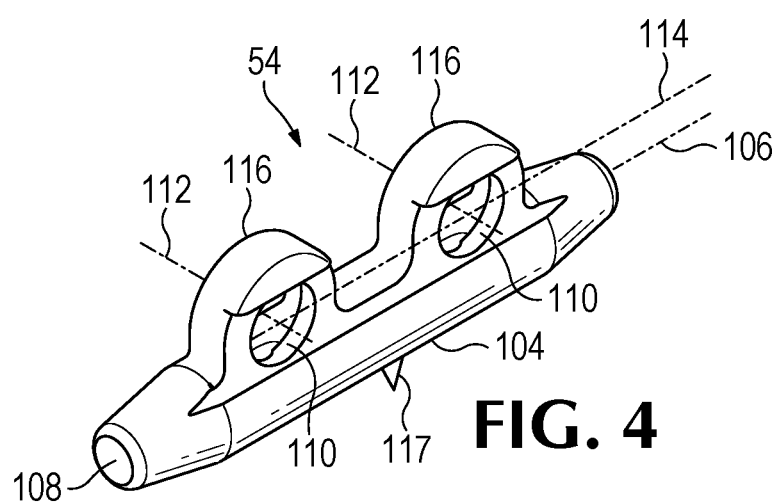
FIG. 4 is an isometric view of the coupler of the fixation apparatus of FIG. 1, taken in isolation from other apparatus components and bone.
Figure 5:
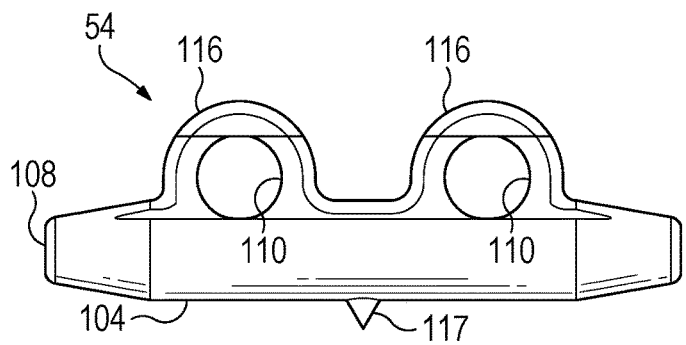
FIG. 5 is a front view of the coupler of FIG. 4.
Figure 8:
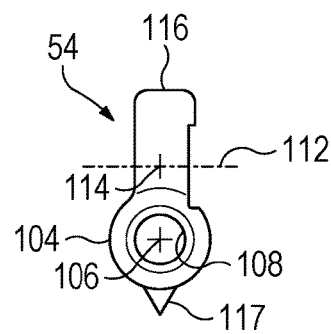
FIG. 8 is an end view of the coupler of FIG. 4.
Figure 6:
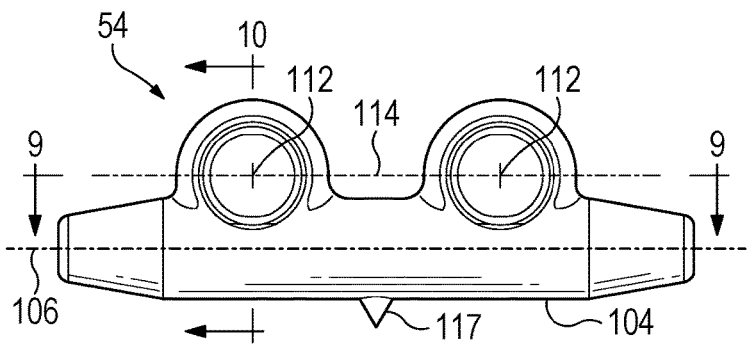
FIG. 6 is a back view of the coupler of FIG. 4.

FIGS. 1-3 show fixation apparatus 50 installed on and stabilizing a left femur 58 having a fracture 60 associated with greater trochanter 62 thereof. Femur 58 also may have sustained one or more other fractures, such as a fracture of femoral shaft 64 that is spanned by plate 52. Each of a head 66 and/or a neck 68 of the femur may be natural or prosthetic. If prosthetic, the head and/or neck may be provided by a prosthesis having a stem extending longitudinally in the medullary canal of the bone. In other embodiments, the fixation apparatus may be installed on any other suitable bone, such as a long bone, having a fracture or other discontinuity amenable to stabilization using flexible members.

Plate 52 may define a plurality of openings 70 configured to receive fasteners, such as bone screws 72 and/or one or more encircling members 74a-74c, among others, that mount the plate to bone. Each opening 70 may or may not be a through-hole extending through the plate, such as between a top surface 76 (interchangeably termed an outer surface) and a bottom surface 78 (interchangeably termed an inner surface). The through-hole may be circular or may be elongated to form a slot. Each through-hole may or may not be configured to be locked to a fastener received in the through-hole. For example, the through-hole may define an internal thread that is complementary to an external thread of a bone screw 72. In other cases, the through-hole may be configured to receive and engage the end of a flexible member 56a-56c or encircling member 74a-74c, and optionally may be deformable to lock the end of the member to the plate at the through-hole.

The plate may be formed integrally as a single plate member or may be composed of at least two plate members 80, 82 that are configured to overlap one another when mounted to a bone. For example, in the depicted embodiment, a pair of plate members collectively form a plate assembly of adjustable length. Overlying plate member 80 defines a recess 84 in which a complementary end portion of underlying plate member 82 is received.

Overlying plate member 80 may define a pair of slots 86a, 86b that can be aligned with internally threaded openings 70 of underlying plate member 82 (see FIGS. 1 and 2). Set screws 88, optionally associated with washers 90, may extend through the respective slots 86a, 86b and into threaded engagement with underlying plate member 82, to lock the plate members to one another with a suitable extent of axial overlap. Each set screw 88 may be long enough to extend into bone under plate 52, as shown in the depicted embodiment (see FIG. 2), or may be shorter, such that the set screw does not substantially enter bone.

A surgeon may select a suitable length for underlying plate member 82 from a set of plate members of different length. Plate 52 may overlap any suitable portion of the length of the bone, such extending to at least the mid-shaft or to opposite ends of the bone's shaft.

Plate 52 may have a head 92 forming an end portion of the plate and extending from the plate's body 94 (see FIGS. 2 and 3). Head 92 may be offset from a plane in which body 94 lies, to follow the contour of the bone past the shaft thereof. For example, in the depicted embodiment, head 92 has an inner surface that is generally complementary to greater trochanter 62. Head 92 may or may not be wider than an average width of body 94.

Head 92 may define an opening 96 extending between plate surfaces 76, 78 (see FIGS. 1-3). Opening 96 may have a circumferentially-bounded perimeter to form a window, as in the depicted embodiment, or may be open at one end (e.g., see Example 3). The head may define a plurality of openings 70 for receiving bone screws 72, one or more flexible members 56a-56c, and/or one or more encircling members 74a-74c (see FIGS. 1-3).

Each encircling member 74a-74c (and each flexible member 56a-56c) may include a pliant element 98 (e.g., a wire or cable) that is tensioned during installation. The encircling member may be configured to extend completely around the bone, either alone (e.g., encircling members 74a and 74c) or collectively with plate 52 (e.g., encircling member 74b). Accordingly, the encircling member may traverse the width of the plate on a path that extends through holes (e.g., encircling member 74a) and/or into surface indentations (e.g., encircling member 74c) of the plate. Opposite ends of the encircling member (e.g., encircling members 74a and 74c) may be held by the same locking member 100, such as a crimp member, that is separate from plate 52 and coupler 54. This arrangement can hold the encircling member in a tensioned configuration. Alternatively, the opposite ends may be engaged with plate 52 to hold the member (e.g., encircling member 74b) in a tensioned configuration. For example, the encircling member may include pliant element 98 and a respective stop member 102 attached to each end thereof. Each stop member may be locked to the pliant element by deformation (i.e., crimping) during installation of the fixation apparatus, or may be pre-attached to the pliant element (such as during manufacture of the fixation apparatus). The stop member is configured to be engaged with the plate at an opening thereof sized to prevent the stop member from passing through.

Coupler 54 may be located on an end region of the bone and spaced from plate 52. In some embodiments, coupler 54 may be disposed anatomically proximal or distal to the shaft of the bone and/or plate 52 (see FIG. 3). Accordingly, the coupler may be located closer to one of the opposite ends of the bone than the plate. For fixation of a discontinuity associated with greater trochanter 62, as in the depicted embodiment, coupler 54 may be positioned on femoral neck 68, such as at a base thereof, and next to the greater trochanter. The coupler may be located on the opposite side of fracture 60 (or a corresponding cut) from the greater trochanter, on a larger piece of the femur, and thus separated from a smaller (trochanter) fragment produced by the discontinuity.

The coupler may be structured to couple two or more flexible members (e.g., flexible members 56a-56c) to one another (see FIGS. 3-10). Coupler 54 may include an elongated barrel 104 defining a longitudinal axis 106. (The barrel is interchangeably called a tube.) The barrel may define a bore 108 extending along axis 106. The barrel may be rounded in cross-section (e.g., having an external cylindrical shape) along at least a portion or at least a majority of the length of the barrel. In other cases, the barrel may be polygonal (e.g., rectangular) in cross-section along at least a portion or at least a majority of the length of the barrel (e.g., see Example 1). The barrel may taper to its opposite ends.

Figure 9:
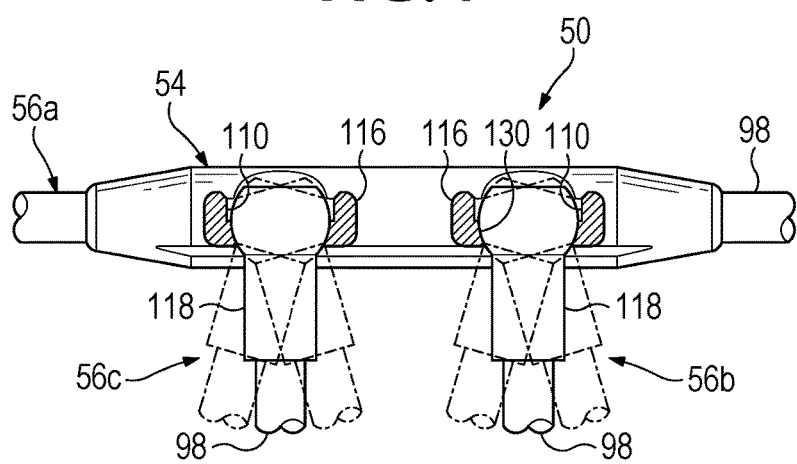
FIG. 9 is a fragmentary, partially sectional view of the fixation apparatus of FIG. 1, taken generally along line 9-9 of FIG. 6, with an exemplary permitted range of motion of two transverse flexible members of the apparatus illustrated in phantom outline.
Figure 11:
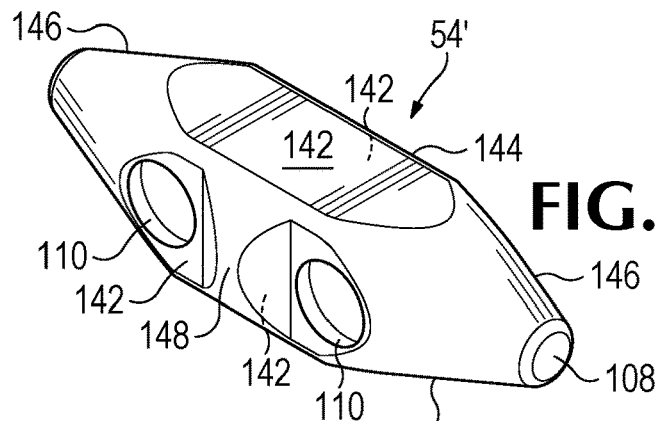
FIG. 11 is an isometric view of a second exemplary coupler for the fixation apparatus of FIG. 1.
Figure 12:
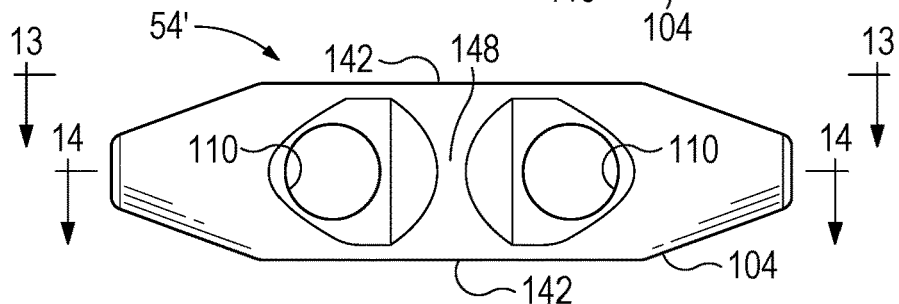
FIG. 12 is a front view of the coupler of FIG. 11.
Figure 13:
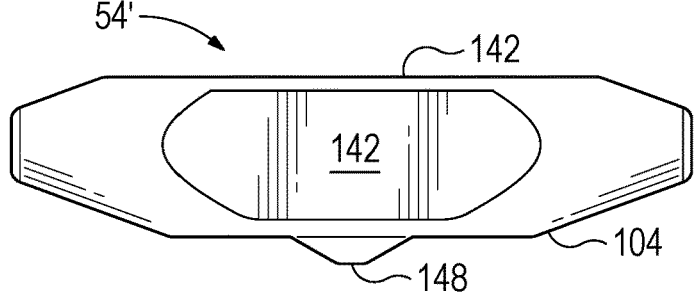
FIG. 13 is a top view of the coupler of FIG. 11.

Pliant element 98 of one of the flexible members (e.g., longitudinal flexible member 56a) may extend longitudinally through coupler 54 via bore 108 (see FIGS. 3 and 9). Flexible member 56a may be tensioned such that coupler 54 is urged against bone, to restrict movement of the coupler, thereby allowing the coupler to function as an anchor for the end (or central region) of one or more other flexible members (such as transverse flexible members 56b and 56c) that approach the coupler transverse to longitudinal axis 106.

Coupler 54 also may define one or more apertures 110 each having a respective through-axis 112 that is transverse to a respective line 114 parallel to longitudinal axis 106 (see FIGS. 4-10). In the depicted embodiment, through-axis 112 is orthogonal to line 114, while in other embodiments, the through-axis may be oriented obliquely to line 114 at any suitable angle. One or more of the flexible members (e.g., flexible members 56b, 56c) may extend into (and, optionally, through) one or more apertures 110. In the depicted embodiment, each transverse flexible member 56b, 56c extends into a separate aperture 110. In other embodiments, only one transverse flexible member may extend through a single aperture 110 or a pair of apertures 110, or may be looped around the outside of the coupler (see Example 2).

Each aperture 110 may be defined by any suitable portion of the coupler. In the depicted embodiment, coupler 54 has a pair of projections 116 that project laterally from barrel 104 intermediate ends thereof, and each projection 116 forms an eyelet defining one of apertures 110. In other embodiments, the same projection 116 may define both apertures 110, barrel 104 may define at least one or each aperture 110 (see Example 1), and/or barrel 104 and projection(s) 116 may cooperatively define at least one and/or each aperture 110 (see Example 2).

The coupler may have one or more surface features projecting from barrel 104 for insertion into bone, to resist slippage of the coupler. For example, the coupler may define at least one spike 117, which may project radially from the barrel. Each spike may project from the bottom of barrel 104, such as from a bottom side of the barrel opposite projections 116 (if present in the coupler).

FIG. 3 shows further aspects of flexible members 56a-56c. Each of the flexible members may be structured, and coupled to plate 52 and coupler 54, as described above for encircling members 74a-74c. The flexible member may be engaged (slidably or locked) with plate 52 and coupler 54. Each flexible member may include a pliant element 98 and a respective stop member 102 pre-attached (e.g., during manufacture) or intra-operatively attached to each end of the pliant element. At least one or each stop member may be a crimp member 118 that is locked to an end of the pliant element, such as intra-operatively, by crimping the crimp member. In some embodiments, at least one end of the pliant element may be locked to the plate or coupler by deformation of an integrally formed locking member of the plate or coupler. In some embodiments, at least one flexible member (e.g., flexible member 56a) may extend through the coupler and over/through the plate, and may have both of its ends secured to the same locking member 100.

Longitudinal flexible member 56a may extend from plate 52, through bore 108 of coupler 54, and back to the plate. Pliant element 98 of flexible member 56a may remain slidable in bore 108, or the pliant element may be locked to the coupler by deformation of barrel 104 and/or through use of a separate fastener that attaches to the barrel. Opposite ends of flexible member 56a may include crimp members 118 (as stop members 102) locked to pliant element 98 and located in plate eyelets 120a, 120b (such as oblique openings), to maintain flexible member 56a in a tensioned configuration. Each oblique opening may have a top end (closer to outer surface 76) and a bottom end (closer to inner surface 78) of plate 52 (see FIGS. 1-3). The bottom end, relative to the top end, may be closer to head 92 of plate 52, to direct flexible member 56a from plate 52 generally toward the head end of the plate and generally away from the opposite end of the plate. Flexible member 56a may secure coupler 54 on the bone and may not bridge fracture 60 (also see FIG. 2). The flexible member may extend to coupler 54 from opposite edges of plate 52 (see FIG. 1).

Transverse flexible members 56b, 56c may extend separately from plate 52 to coupler 54 (see FIGS. 1 and 3). More specifically, flexible members 56b, 56c may extend from respective plate eyelets 122a, 122b (e.g., parallel openings) to respective apertures 110 of coupler 54 (see FIG. 3). Optionally, the paths of the flexible members may cross one another, as depicted. The opposite ends of each flexible member 56b, 56c may include stop members 102, such as crimp members 118, that engage respective plate eyelets 122a, 122b and respective apertures 110 to maintain each flexible member in a tensioned configuration. Plate eyelets 122a, 122b may be oriented parallel to local top and bottom surface regions of the plate, and may be defined by tabs 124 projecting into opening 96. At least one or each flexible member 56b, 56c may bridge fracture 60. In the depicted embodiment, flexible members 56b, 56c restrict proximal movement of a greater trochanter fragment encouraged by action of abductor muscles.

Figure 10:
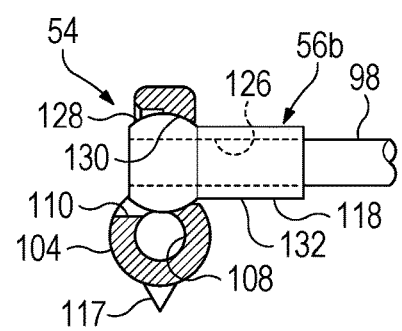
FIG. 10 is another fragmentary, partially sectional view of the fixation apparatus of FIG. 1, taken generally along line 10-10 of FIG. 6.
Figure 7:
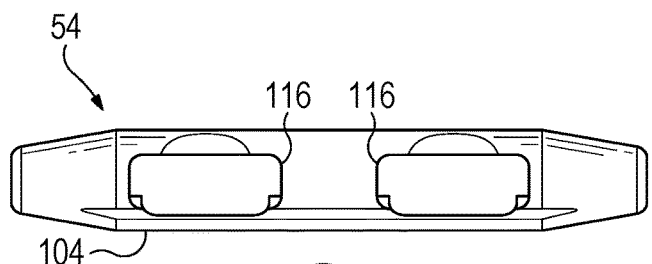
FIG. 7 is a top view of the coupler of FIG. 4.

FIGS. 9 and 10 illustrate further exemplary aspects of crimp members 118 and apertures 110. Each crimp member 118 may define a hole 126 (e.g., a through-hole) sized to receive a section of pliant element 98. The crimp member may have a spherical region 128 (interchangeably termed a head) that interfaces with a complementary spherical wall region 130 of aperture 110 (or with a complementary wall of any of the eyelets defined by plate 52). The spherical region has a diameter greater than the minimum diameter of aperture 110 (or a plate eyelet), and thus prevents passage of the crimp member completely through the aperture (or plate eyelet). A deformable region 132 of the crimp member, interchangeably termed a shaft, projects from spherical region 128. The deformable region may have a diameter that is less than the minimum diameter of the aperture (or plate eyelet), and/or may be cylindrical. The deformable region can be crimped to lock the crimp member to an end of pliant element 98.

The spherical interface formed between crimp member 118 and the wall of aperture 110 (or a plate eyelet) permits swiveling of the crimp member to change the orientation of the through-axis of hole 126, as indicated in phantom outline in FIG. 9 (also see FIG. 10). This swiveling may reduce the bending moment applied to the flexible member, particularly at the junction where pliant element 98 enters a crimp member 118, which may decrease fatigue or failure of the pliant element at this junction. The pivotal motion also may facilitate placement of the coupler under soft tissue during installation of the fixation apparatus, after an end of each flexible member 56b, 56c has been coupled to the coupler via a crimp member 118. Any suitable range of pivotal motion may be permitted in a plane by the interface, such as a change of orientation in the plane of at least about 30, 45, 60, or 90 degrees, among others.

The fixation apparatus may function as a tension band to stabilize a discontinuity associated with a process (e.g., the greater trochanter) near or at the end of a bone. Tensioned transverse flexible members may apply compression to the process, orthogonal to the discontinuity, which may restrict motion of the process. Increased tension generated by muscle action results in increased compression across the discontinuity.

II. Methods of Bone Fixation

This section describes exemplary methods of bone fixation using apparatus of the present disclosure. The method steps of this section may be performed in any suitable order and combination, and may be modified by, or combined with, any other suitable aspects of the present disclosure.

A bone to be fixed may be selected. The method may be performed on any suitable bone, and on any suitable portion thereof, such as a proximal portion, a central portion, a distal portion, or a combination thereof, among others. Exemplary bones that may be selected include a long bone of a limb, such as a femur, tibia, fibula, humerus, radius, or ulna. The bone may have any suitable discontinuity, such as at least one fracture, cut, nonunion, or the like. The discontinuity may be associated with a process of the bone located near the end of the bone. The process may, for example, be a greater trochanter or an olecranon, among others. The discontinuity may intersect the process or may be located near but outside the process. The discontinuity may form a fragment of the bone, with the fragment including at least a portion of the process.

An incision may be created through overlying soft tissue to access the selected bone. The bone may be manipulated to reposition bone fragments (e.g., to approximate the relative anatomical position of the fragments), such as to set a fracture. Manipulation of bone fragments may be performed before and/or after the incision is created.

A plate may be selected for stabilizing the bone. The plate may be elongated and/or may have any combination of the plate features described elsewhere herein. The plate may be placed through the incision and onto the bone, optionally such that the plate bridges at least one discontinuity in the bone. The at least one discontinuity may include the discontinuity associated with the process, as described above.

The plate may be attached to the bone with one or more fasteners, such as at least one screw, peg, pin, wire, cable, rivet, and/or the like. Each fastener may extend into bone directly under the plate from an opening thereof (e.g., in the case of a screw, peg, or pin), or may extend through/over the plate and through/around the bone (e.g., in the case of a wire or cable). The fastener may engage the plate, and may or may not lock to the plate, such as via threaded engagement. In some embodiments, the plate may be attached provisionally to the bone with at least one tool, such as at least one clamp, before the plate is attached with the one or more fasteners and/or one or more encircling members.

A coupler may be selected for use with the plate. The coupler may have any suitable combination of the features described herein. The selected coupler may be disposed on the selected bone, optionally closer than the plate to an end of the bone. The coupler may be placed onto or adjacent the process near the end of the bone.

One or more flexible members may be coupled to the coupler before or after the coupler has been disposed on the bone. For example, before the coupler is disposed on the bone, an end of a pliant element of a first flexible member may be fed through a longitudinal bore of the coupler, an end of a pliant element of a second flexible member (and optionally a third flexible member) may be fed through an aperture of the coupler, and/or a pliant element of a second flexible member may be looped around the outside of the coupler. The pliant element may have a stop member (e.g., a crimp member) pre-attached to an end thereof, or the stop member may be attached after the end of the pliant element has been fed through the aperture.

Each flexible member may be coupled to the plate at only one end or both ends, or at a position intermediate the ends, using a stop member (e.g., a crimp member) of the flexible member or a locking member. The stop member or locking member may be locked to an end or both ends of a pliant element of the flexible member before or after the pliant element has been tensioned.

III. Composition of Apparatus Components

Each plate, coupler, pliant element, locking member, stop member, and crimp member of the present disclosure may have any suitable composition. Each may be formed independently, and at least partially or completely of any suitable biocompatible material(s) and/or bioresorbable (bioabsorbable) material(s). Illustrative biocompatible materials that may be suitable include (1) metal (for example, titanium or titanium alloy, cobalt-chrome alloy, stainless steel, etc.); (2) polymer/plastic (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) bioresorbable material or polymer/plastic (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.)); (4) bone material or bone-like material (e.g., bone chips, calcium phosphate crystals (e.g., hydroxyapatite, carbonated apatite, etc.)); or (5) any combination thereof. In some embodiments, each component of the apparatus is formed of metal. In some embodiments, each component of the apparatus is formed of polymer. In some embodiments, each pliant member is formed of metal, each crimp member is formed of metal, the plate is formed of metal or polymer, and the coupler is formed of metal or polymer.

IV. Examples

The following examples describe selected embodiments of the apparatus and methods of the present disclosure. These examples are intended to illustrate aspects and features of the apparatus and methods and should not limit the scope of the disclosure.

Example 1. Coupler with Contiguous Openings for Flexible Members

This example describes an exemplary coupler 54' for a fixation apparatus 50'; see FIGS. 11-15. The coupler of this example may have any suitable combination of coupler features disclosed elsewhere herein, such as disclosed in the examples below and/or in Section I.

The coupler may include a barrel 104 defining one or more flats 142 (planar side regions), which may help to stabilize the position and/or orientation of the coupler on bone. For example, in the depicted embodiment, the flats of the coupler form a rectangular mid-section 144 intermediate a pair of conical end sections 146. A raised member 148 projecting from one of flats 142 may provide a visual and haptic landmark for the surgeon, to facilitate properly orienting the coupler.

Figure 14:
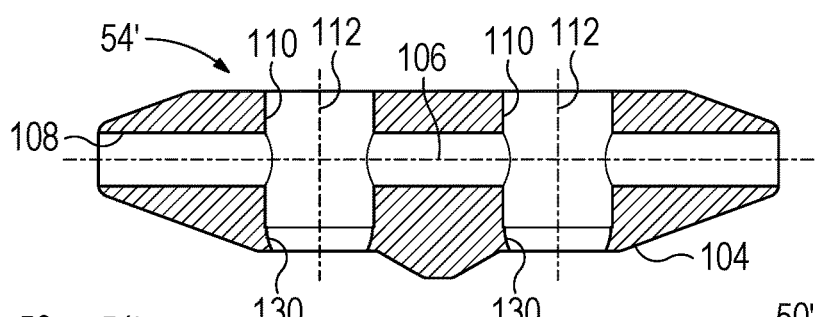
FIG. 14 is a sectional view of the coupler of FIG. 11, taken generally along line 14-14 of FIG. 12.
Figure 15:
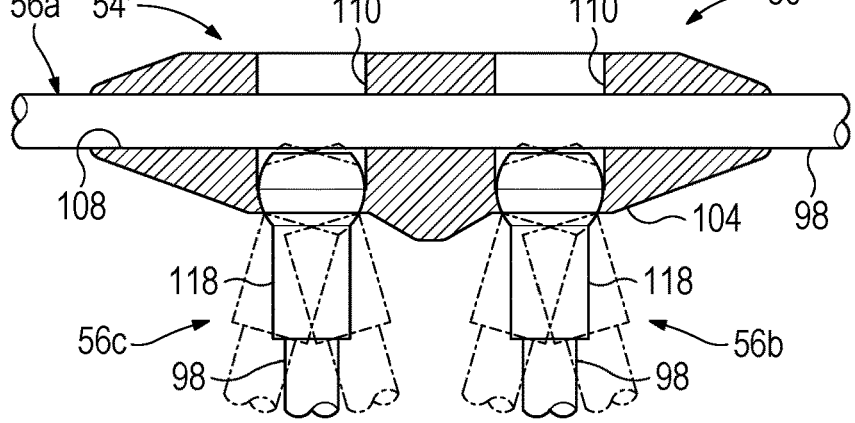
FIG. 15 is a fragmentary, partially sectional view of an exemplary fixation apparatus corresponding to that of FIG. 1, except utilizing the coupler of FIG. 11, taken as in FIG. 14, with an exemplary permitted range of motion of two transverse flexible members of the fixation apparatus illustrated in phantom outline.

The coupler may define a longitudinal bore 108 and a pair of transverse apertures 110 that intersect the bore (see FIGS. 14 and 15). Each transverse aperture 110 may extend transversely, such as orthogonally to bore 108, through barrel 104. The aperture may narrow toward one end, to form a spherical wall region 130 that is complementary to a spherical region of crimp member 118, as described above in Section I, to allow the crimp member to swivel, as shown in FIG. 15.

Example 2. Couplers for a Single Transverse Flexible Member

This example describes exemplary couplers for use in fixation apparatus 50 or 50' in place of coupler 54 or 54', with only a single transverse flexible member; see FIGS. 16-21. Each of the couplers of this example may have any suitable combination of features disclosed elsewhere herein, such as in Section I and Example 1.

Figure 16:
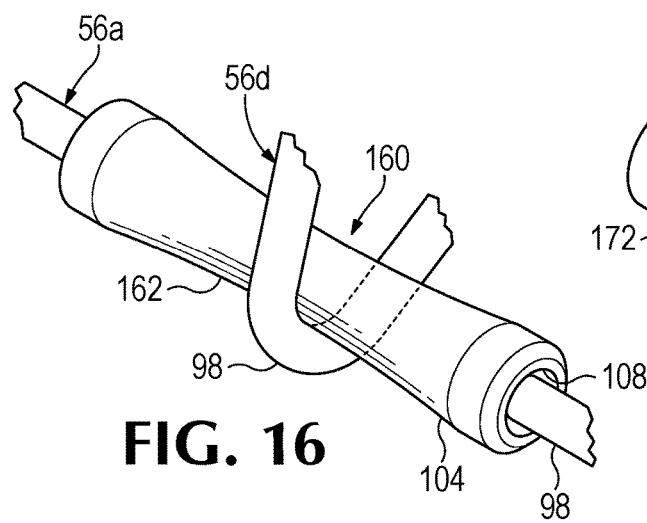
FIG. 16 is a fragmentary view of another exemplary fixation apparatus corresponding to that of FIG. 1, except utilizing a third exemplary coupler defining no transverse apertures.

FIG. 16 shows an exemplary coupler 160 including a barrel 104 defining a longitudinal bore 108 and having an outer diameter that decreases centrally along the barrel. Coupler 160 may slidably receive a section of longitudinal flexible member 56a in longitudinal bore 108, as described above in Section I for coupler 54. However, coupler 160 may not define a transverse aperture(s) for receiving a portion of one or more transverse flexible members. Instead, barrel 104 may define a depression 162 intermediate the opposite ends of the barrel to receive a portion of a transverse flexible member 56d. The transverse flexible member 56d may extend in a circumferential direction around the outside of the barrel about one-half turn, such that the flexible member doubles back toward the plate. In some embodiments, the transverse flexible member may be wound around the outside of the barrel an additional one or more full turns before extending back to the plate. In some embodiments, the barrel may define a narrower depression, such as a circumferential groove to receive a portion of the transverse flexible member.

Figure 17:
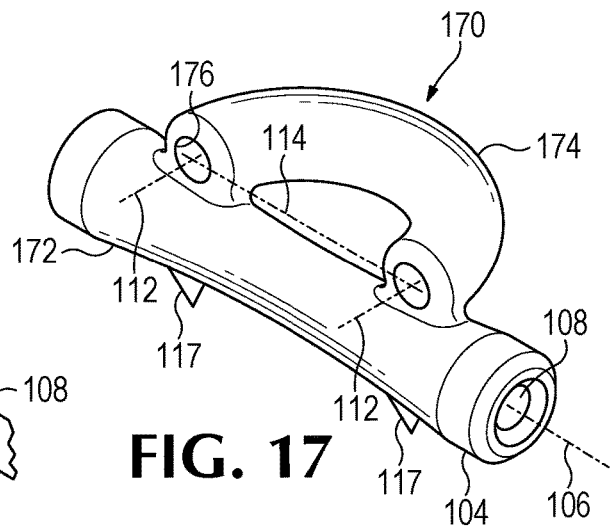
FIG. 17 is an isometric view of a fourth exemplary coupler for a fixation apparatus corresponding to that of FIG. 1.

FIG. 17 shows an exemplary coupler 170 including first and second tubes 172, 174 that are rigidly attached to one another. First tube 172 may form a linear barrel 104 and thus may slidably receive a section of a longitudinal flexible member in longitudinal bore 108, as described above in Section I for coupler 54. Second tube 174 may be arcuate, to define a curved aperture 176 for receiving a section of a transverse flexible member, such that the flexible member generally doubles back toward the plate. Accordingly, the transverse flexible member may extend from opposite ends of second tube 174 in respective directions that are transverse to a line 114 that is parallel to longitudinal axis 106. Coupler 170 also may have one or more spikes 117 arranged on first tube 172 generally opposite the attachment sites for second tube 174.

Figure 18:
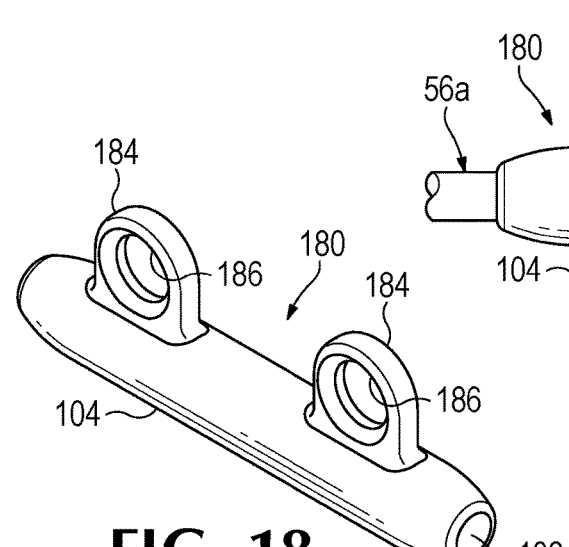
FIG. 18 is an isometric view of a fifth exemplary coupler for a fixation apparatus corresponding to that of FIG. 1.
Figure 19:
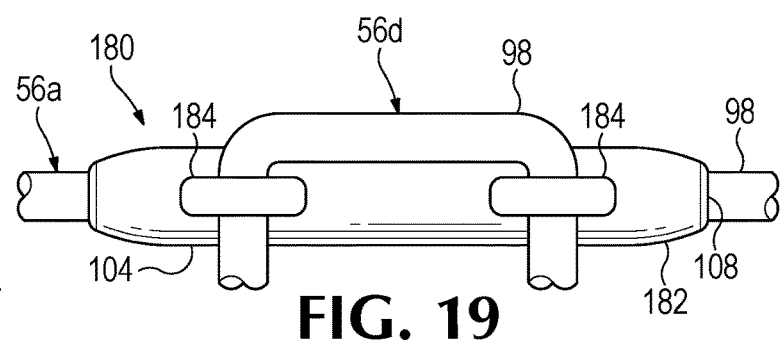
FIG. 19 is a fragmentary view of a fixation apparatus corresponding to that of FIG. 1, except utilizing the coupler of FIG. 18.

FIGS. 18 and 19 show an exemplary coupler 180 including a tube 182 and a pair of eyelets 184 protruding therefrom and defining respective transverse apertures 186. In FIG. 19, a longitudinal flexible member 56a extends through tube 182, and a transverse flexible member 56d extends from a plate (not shown) through each eyelet and back to the plate. The transverse flexible member may be connected to the plate at both ends with crimp members, as described in Section I for flexible member 56a, or may have its ends secured with a stop member, as described in Section I for encircling members 74a, 74c.

Figure 20:
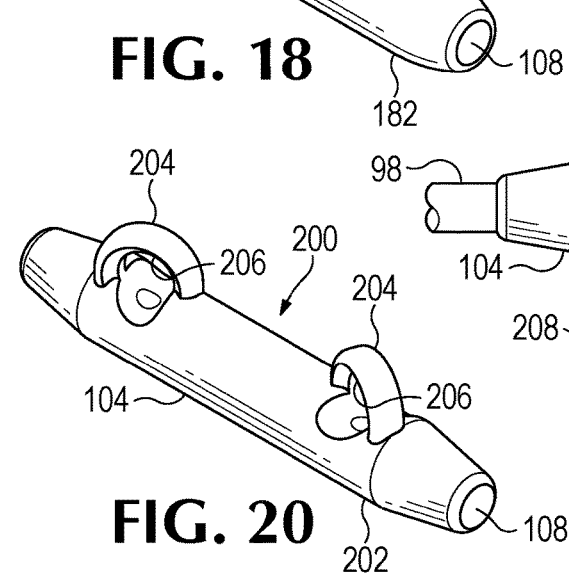
FIG. 20 is an isometric view of a sixth exemplary coupler for a fixation apparatus corresponding to that of FIG. 1.
Figure 21:
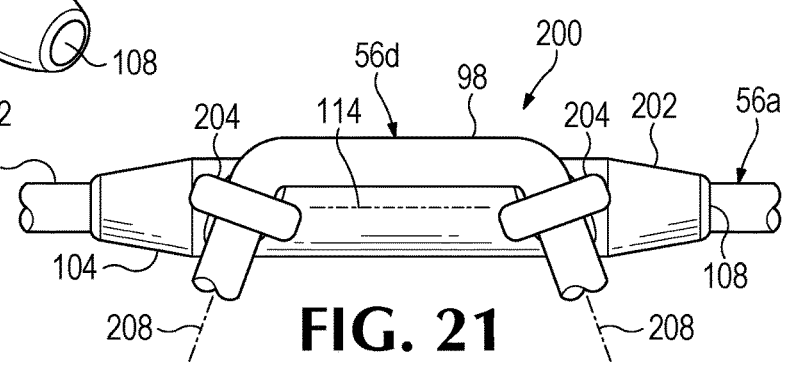
FIG. 21 is a fragmentary view of a fixation apparatus corresponding to that of FIG. 1, except utilizing the coupler of FIG. 20.

FIGS. 20 and 21 show an exemplary coupler 200 including a tube 202 and a pair of arched projections 204 protruding therefrom. Tube 202 and projections 204 cooperatively define transverse apertures 206, which have through-axes 208 arranged obliquely to line 114. In FIG. 21, a longitudinal flexible member 56a extends through tube 202, and a transverse flexible member 56d extends from a plate (not shown) through each aperture 206 and back to the plate. The transverse flexible member may be secured as described for coupler 180.

Example 3. Open-Ended Plate

Figure 22:
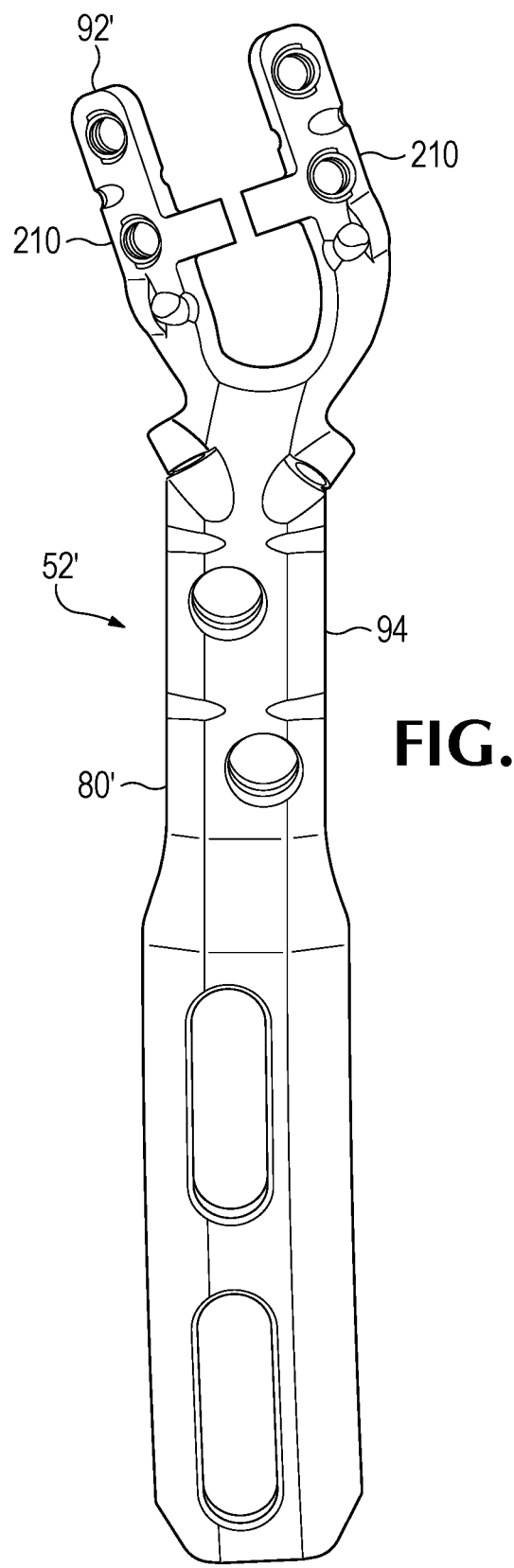
FIG. 22 is a plan view of another exemplary plate member for the fixation apparatus of FIG. 1.

This example describes an exemplary open-ended plate 52' for the fixation apparatus of the present disclosure; see FIG. 22.

FIG. 22 shows only a portion of plate 52', namely, an alternative overlying plate member 80' thereof (compare with plate member 80 of FIG. 1). Plate member 80' has a head 92' forming a pair of arms 210. The arms extend separately from a body 94 of plate 52'. Each arm may define a respective long axis that is oblique to the long axis of body 94, when the plate is projected onto a plane as in FIG. 22. Head 92' may have any suitable combination of features described above for head 92, and alternatively may be utilized in a one-piece plate.

Example 4. Olecranon Fixation Apparatus

Figure 23:
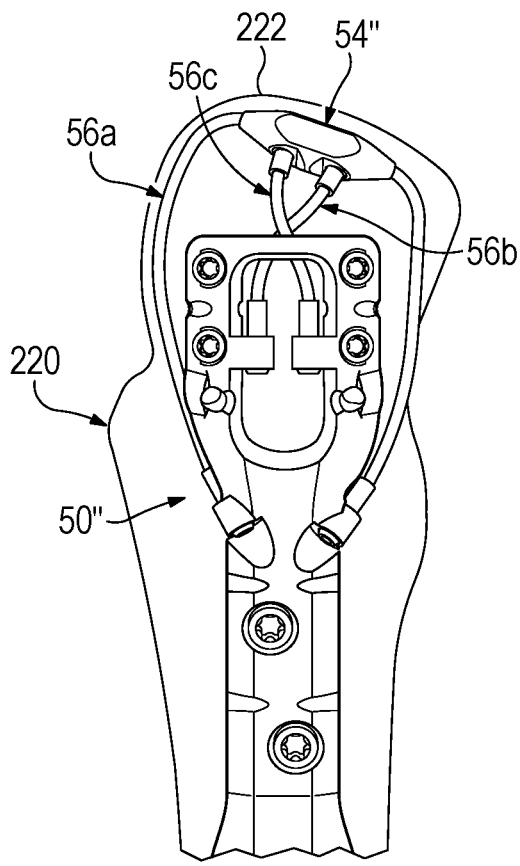
FIG. 23 is a fragmentary view of the fixation apparatus of FIG. 1 installed on and fixing a proximal portion of a fractured ulna, taken with a posterior view of the ulna.
Figure 24:
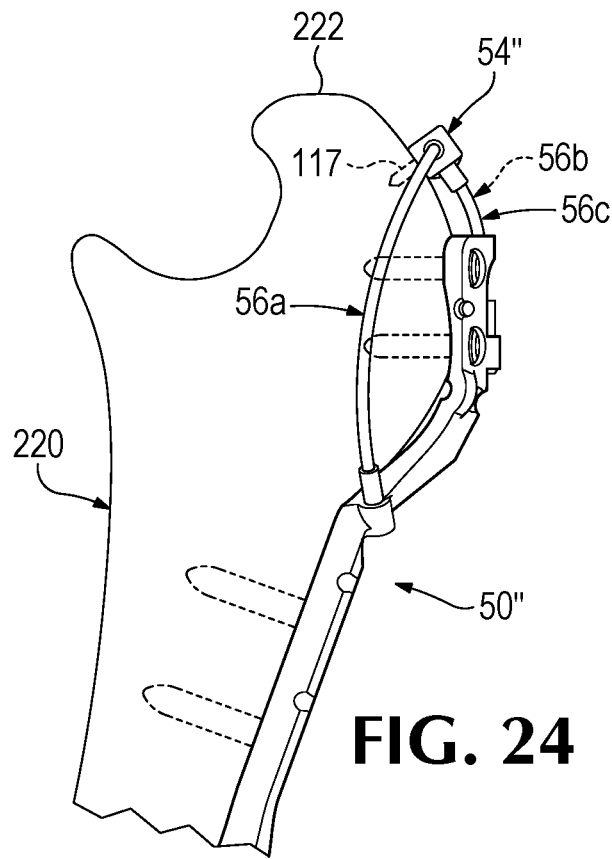
FIG. 24 is another fragmentary view of the fixation apparatus and ulna of FIG. 23, taken with a lateral view of the ulna.

This example describes use of a fixation apparatus 50" for fixation of a proximal end portion of an ulna 220; see FIGS. 23 and 24.

Fixation apparatus 50" is shown with a coupler 54" similar to coupler 54', except having a spike 117 inserted into olecranon 222 of the ulna.

Example 5. Selected Embodiments

This example describes selected embodiments of the present disclosure, presented as a series of indexed paragraphs.

Paragraph A1. A method of fixing a bone, the method comprising, in any order: (a) attaching a plate to a shaft region of the bone; (b) disposing a coupler on an end region of the bone; and (c) connecting the coupler to the plate with (i) a first flexible member extending from the plate, through a bore of the coupler, and back to the plate, and (ii) a second flexible member or second and third flexible members each extending from the plate to the coupler on a path that approaches the coupler transverse to a line that is parallel to the bore, wherein each of the first and second or first, second, and third flexible members includes a wire or cable.

Paragraph A2. The method of paragraph A1, wherein the plate has a pair of opposite edges, and wherein the first flexible member extends to the coupler from each opposite edge of the pair of opposite edges of the plate.

Paragraph A3. The method of paragraph A2, wherein the plate has a pair of opposite ends, and wherein the second flexible member or each of the second and third flexible members extends to the coupler from the same opposite end of the plate.

Paragraph A4. The method of any one of paragraphs A1 to A3, wherein the second flexible member or each of the second and third flexible members extends longitudinally from the plate.

Paragraph A5. The method of any one of paragraphs A1 to A4, wherein the plate has a first end opposite a second end, wherein the first end is closer than the second end to the coupler, wherein the first flexible member, relative to the second flexible member or the second and third flexible members, is coupled to the plate farther from the first end.

Paragraph A6. The method of any one of paragraphs A1 to A5, wherein the plate defines a first pair of openings at which the first flexible member is coupled to the plate and a second pair of openings at which the second flexible member or each of the second and third flexible members is coupled to the plate, wherein the first pair of openings define through-axes that are not parallel to one another (and optionally not parallel to a plane orthogonal to a longitudinal axis of the plate), and wherein the second pair of openings define through-axes that are more parallel to one another than the through-axes of the first pair of openings are to one another.

Paragraph A7. The method of any one of paragraphs A1 to A6, wherein the step of disposing includes a step of disposing the coupler on the femoral neck of a femur, next to the greater trochanter of the femur.

Paragraph A8. The method of paragraph A7, wherein the first flexible member extends over anterior and posterior sides of the greater trochanter of the femur, and wherein the second flexible member or each of the second and third flexible members extends over a lateral side of the greater trochanter.

Paragraph A9. The method of paragraph A7 or paragraph A8, wherein the plate bridges a discontinuity of the greater trochanter.

Paragraph A10. The method of any one of paragraphs A1 to A9, wherein the second flexible member or each of the second and third flexible members bridges a discontinuity of the bone.

Paragraph A11. The method of paragraph A10, wherein the first flexible member does not bridge the discontinuity of the bone.

Paragraph A12. The method of paragraph A10 or A11, wherein the discontinuity intersects the greater trochanter of a femur.

Paragraph A13. The method of any one of paragraphs A1 to A12, wherein the second and third flexible members extend on paths that cross one another between the plate and the coupler.

Paragraph A14. The method of any one of paragraphs A1 to A12, wherein the second flexible member extends from the plate to the coupler and back to the plate, and optionally bridges a discontinuity of the bone twice.

Paragraph A15. The method of any one of paragraphs A1 to A6, A10, A11, A13, and A14, wherein the step of attaching a plate includes a step of attaching the plate to a shaft region of an ulna, and wherein the step of disposing a coupler includes a step of disposing the coupler on the olecranon of the ulna.

Paragraph A16. The method of any one of paragraphs A1 to A15, wherein the step of connecting includes a step of locking a respective crimp member to the wire or cable of each flexible member of the first and second, or first, second, and third flexible members.

Paragraph A17. The method of paragraph A16, wherein the respective crimp member is at least partially located in an aperture of the plate or the coupler when such crimp member is locked to the wire or cable of the flexible member.

Paragraph A18. The method of paragraph A16 or paragraph A17, wherein the step of locking a respective crimp member is performed while the wire or cable of the flexible member is under tension.

Paragraph A19. The method of any one of paragraphs A1 to A18, wherein the second flexible member or each of the second and third flexible members forms a slidable interface with the coupler.

Paragraph A20. The method of paragraph A19, wherein the slidable interface is spherical.

Paragraph A21. The method of any one of paragraphs A1 to A20, wherein the coupler defines a pair of apertures, and wherein the step of connecting includes a step of connecting the plate to the coupler using the second flexible member and a third flexible member each extending into a different aperture of the pair of apertures on a respective path that approaches the coupler transverse to a line that is parallel to the bore.

Paragraph A22. The method of paragraph A21, wherein the pair of apertures do not communicate with the bore.

Paragraph A23. The method of paragraph A21, wherein each aperture of the pair of apertures communicates with the bore.

Paragraph A24. The method of any one of paragraphs A1 to A23, wherein none of the flexible members is locked to the coupler.

Paragraph A25. The method of any one of paragraphs A1 to A24, wherein the first flexible member includes enlarged end portions that engage the plate at a pair of openings thereof.

Paragraph A26. The method of any one of paragraphs A1 to A25, wherein the coupler is only one piece.

Paragraph A27. The method of any one of paragraphs A1 to A26, wherein the coupler includes a spike configured to be driven into the bone.

Paragraph B1. A method of fixing a femur having a fracture associated with the greater trochanter of the femur, the method comprising: (a) attaching a plate to a shaft region of the femur; (b) disposing a coupler on the neck of the femur next to the greater trochanter, the coupler being elongated along a long axis; and (c) connecting the coupler to the plate with (i) a first flexible member extending from the plate, through the coupler, and back to the plate, and (ii) a second flexible member extending from the plate to the coupler on a path that approaches the coupler transverse to a line that is parallel to the long axis, wherein each flexible member of the first and second flexible members includes a wire or cable.

Paragraph B2. The method of paragraph B1, wherein the line is parallel to a bore defined by the coupler, and wherein the first flexible member extends through the bore.

Paragraph B3. The method of paragraph B1 or paragraph B2, wherein the step of connecting the coupler to the plate includes a step of locking a respective crimp member to the wire or cable of each flexible member of the first and second flexible members.

Paragraph B4. The method of any one of paragraphs B1 to B3, wherein the coupler defines a pair of apertures, and wherein the step of connecting the coupler to the plate includes a step of connecting the coupler to the plate using the second flexible member and a third flexible member each extending into a different aperture of the pair of apertures on a respective path that approaches the coupler transverse to a line that is parallel to the long axis.

Paragraph B5. The method of paragraph B4, wherein each of the second flexible member and the third flexible member engages the coupler at a respective spherical interface.

Paragraph B6. The method of any one of paragraphs B1 to B5, further comprising any limitation or combination of limitations from one or more of paragraphs A1 to A27.

Paragraph C1. An apparatus for fixing a bone, comprising: (a) a plate defining a plurality of openings configured to receive fasteners that attach the plate to a shaft region of the bone; (b) a coupler configured to be disposed on an end region of the bone, the coupler defining a bore and an aperture; (c) a first flexible member including a wire or cable and a crimp member; and (d) a second flexible member including a wire or cable and a crimp member; wherein the coupler and the plate are configured to be connected to one another using (i) the first flexible member extending from the plate, through the bore of the coupler, and back to the plate, and (ii) the second flexible member extending from the plate to the aperture of the coupler on a path that approaches the aperture transverse to a line that is parallel to the bore.

Paragraph C2. The apparatus of paragraph C1, the aperture being a first aperture, further comprising a third flexible member including a wire or cable and a crimp member and configured to connect the coupler and the plate to one another using the third flexible member extending from the plate to a second aperture of the coupler on a path that approaches the aperture transverse to a line that is parallel to the bore.

Paragraph C3. The apparatus of paragraph C1 or C2, wherein the aperture or each of the first and second apertures is separate from the bore.

Paragraph C4. The apparatus of paragraph C1 or C2, wherein the aperture or each of the first and second apertures communicates with the bore.

Paragraph C5. The apparatus of any one of paragraphs C1, C3, and C4, wherein the second flexible member is configured to extend from the plate, through the aperture, and back to the plate.

Paragraph C6. The apparatus of any one of paragraphs C1 to C5, wherein the second flexible member includes a pair of crimp members, and wherein each crimp member of the pair of crimp members is locked or lockable to an end of the wire or cable of the second flexible member.

Paragraph C7. The apparatus of any one of paragraphs C1 to C6, wherein the crimp member of the second flexible member is configured to form a spherical interface with the coupler at the aperture.

Paragraph C8. The apparatus of any one of paragraphs C1 to C7, wherein the coupler includes an elongated barrel that defines the bore.

Paragraph C9. The apparatus of any one of paragraphs C1 to C8, wherein the coupler is only one piece.

Paragraph C10. The apparatus of any one of paragraphs C1 to C9, wherein the coupler includes a barrel that defines the bore, and wherein the coupler includes a spike projecting from the barrel and configured to be driven into the bone.

Paragraph C11. The apparatus of any one of paragraphs C1 to C10, wherein the second flexible member, and, optionally, a third flexible member, if present, are configured to extend toward the coupler from the same end of the plate.

Paragraph C12. The apparatus of any one of paragraphs C1 to C11, wherein the plate has a pair of opposite edges, and wherein the first flexible member is configured to extend toward the coupler from each opposite edge of the pair of opposite edges of the plate.

Paragraph C13. The apparatus of any one of paragraphs C1 to C12, wherein the plate has a first end opposite a second end, wherein the first end is configured to be closer than the second end to the coupler, and wherein the first flexible member, relative to the second flexible member, is configured to be coupled to the plate farther from the first end.

Paragraph C14. The apparatus of any one of paragraphs C1 to C13, wherein the plate defines a pair of first openings at which the first flexible member is configured to be connected to the plate and a pair of second openings at which the second flexible member or each of the second member and a third flexible member are configured to be connected to the plate, wherein the first pair of openings define through-axes that are oblique or orthogonal to one another, and wherein the second pair of openings define through-axes that are parallel to one another.

Paragraph C15. The apparatus of any one of paragraphs C1 to C14, further comprising a limitation or combination of limitations from one or more of paragraphs A1 to A27 and B1 to B6.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of fixing a bone, the method comprising:
    attaching a plate to a shaft region of the bone;
    disposing a coupler on an end region of the bone; and
    connecting the coupler to the plate with a first flexible member extending from the plate, through a bore of the coupler, and back to the plate, and with a second flexible member extending from the plate to the coupler on a path that approaches the coupler transverse to a line that is parallel to the bore, wherein each of the first and second flexible members includes a wire or cable.

2. The method of claim 1, wherein the plate has a pair of opposite edges, and wherein the first flexible member extends to the coupler from each opposite edge of the pair of opposite edges of the plate.

3. The method of claim 2, wherein the plate has a pair of opposite ends, and wherein the second flexible member extends to the coupler from one of the opposite ends of the plate.

4. The method of claim 1, wherein the second flexible member extends longitudinally from an end of the plate.

5. The method of claim 1, wherein the plate has a first end opposite a second end, wherein the first end is closer than the second end to the coupler, wherein the first flexible member, relative to the second flexible member, is connected to the plate farther from the first end.

6. The method of claim 1, wherein the plate defines a first pair of openings at which the first flexible member is coupled to the plate and a second pair of openings at which the second flexible member and a third flexible member are coupled to the plate, wherein the first pair of openings define through-axes that are not parallel to one another, and wherein the second pair of openings define through-axes that are more parallel to one another than the through-axes of the first pair of openings are to one another.

7. The method of claim 1, wherein the step of disposing a coupler includes a step of disposing a coupler on the femoral neck of a femur, next to the greater trochanter of the femur.

8. The method of claim 7, wherein the first flexible member extends over anterior and posterior sides of the greater trochanter of the femur, and wherein the second flexible member extends over a lateral side of the greater trochanter.

9. The method of claim 7, wherein each of the plate and the second flexible member bridges a discontinuity of the greater trochanter.

10. The method of claim 1, wherein the second flexible member bridges a discontinuity of the bone.

11. The method of claim 1, wherein the step of connecting includes a step of locking a respective crimp member to the wire or cable of each of the first and second flexible members.

12. The method of claim 1, wherein the second flexible member forms a spherical interface with the coupler.

13. The method of claim 1, wherein the coupler defines a pair of apertures, and wherein the step of connecting includes a step of connecting the coupler to the plate using the second flexible member and a third flexible member each extending into a different aperture of the pair of apertures on a respective path that approaches the coupler transverse to a line that is parallel to the bore.

14. The method of claim 1, wherein neither of the first and second flexible members is locked to the coupler.

15. A method of fixing a femur having a fracture associated with the greater trochanter of the femur, the method comprising:
   attaching a plate to a shaft region of the femur;
   disposing a coupler on the neck of the femur next to the greater trochanter, the coupler being elongated along a long axis; and
   connecting the coupler to the plate with a first flexible member extending from the plate, through the coupler, and back to the plate, and with a second flexible member extending from the plate to the coupler on a path that approaches the coupler transverse to a line that is parallel to the long axis, wherein each flexible member of the first and second flexible members includes a wire or cable.

16. The method of claim 15, wherein the line is parallel to a bore defined by the coupler, and wherein the first flexible member extends through the bore.

17. The method of claim 15, wherein the step of connecting the coupler to the plate includes a step of locking a respective crimp member to the wire or cable of each flexible member of the first and second flexible members.

18. The method of claim 15, wherein the coupler defines a pair of apertures, and wherein the step of connecting the coupler to the plate includes a step of connecting the coupler to the plate using the second flexible member and a third flexible member each extending into a different aperture of the pair of apertures on a respective path that approaches the coupler transverse to a line that is parallel to the long axis.

19. The method of claim 18, wherein each of the second flexible member and the third flexible member engages the coupler at a respective spherical interface.

* * * * *